(12) United States Patent
Jung et al.

(10) Patent No.: US 6,541,178 B2
(45) Date of Patent: Apr. 1, 2003

(54) ION-TYPE PHOTOACID GENERATOR CONTAINING NAPHTHOL AND PHOTOSENSITIVE POLYIMIDE COMPOSITION PREPARED BY USING THE SAME

(75) Inventors: Myung-Sup Jung, Taejeon (KR); Seung-Ju Seo, Taejeon (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 55 days.

(21) Appl. No.: 09/750,033

(22) Filed: Dec. 29, 2000

(65) Prior Publication Data

US 2002/0048719 A1 Apr. 25, 2002

(30) Foreign Application Priority Data

Dec. 29, 1999 (KR) .......................................... 99-64662

(51) Int. Cl.$^7$ .............................................. G03F 7/039
(52) U.S. Cl. ...................... 430/270.1; 430/906; 522/31; 562/30
(58) Field of Search ............................. 430/270.1, 906; 522/31; 562/30

(56) References Cited

U.S. PATENT DOCUMENTS

| | | | |
|---|---|---|---|
| 3,957,512 A | 5/1976 | Kleeberg et al. | 430/325 |
| 4,069,055 A | 1/1978 | Crivello | 430/280.1 |
| 4,069,056 A | 1/1978 | Crivello | 430/287.1 |
| 4,243,743 A | 1/1981 | Hiramoto et al. | 430/287.1 |
| 5,840,467 A * | 11/1998 | Kitatani et al. | 430/157 |
| 5,965,319 A * | 10/1999 | Kobayashi | 430/176 |
| 6,383,714 B1 * | 5/2002 | Nakamura et al. | 101/462 |

FOREIGN PATENT DOCUMENTS

| | | |
|---|---|---|
| JP | 52-13315 | 2/1977 |
| JP | 60-37550 | 2/1985 |
| JP | 62-135824 | 6/1987 |
| JP | 64-18143 | 1/1989 |
| JP | 64-60630 | 3/1989 |
| JP | 1-311103 | 12/1989 |
| JP | 3-154059 | 7/1991 |
| JP | 4-204945 | 7/1992 |
| JP | 5-204154 | 8/1993 |
| JP | 6-73003 | 3/1994 |

OTHER PUBLICATIONS

Omoto et al, "Fluorine–Containing Photoreactive Polyimides . . . " Macromolecules, 23:4796–4802 (1990).
Crivello et al, "Recent Advances in Thermally and Photochemically Initiated Cationic Polymerization", Polymer Journal, 17(1):73–83 (1985).

* cited by examiner

Primary Examiner—John S. Chu
(74) Attorney, Agent, or Firm—Lee & Sterba, P.C.

(57) ABSTRACT

The photoacid generator according to the present invention is represented by the general formula (1):

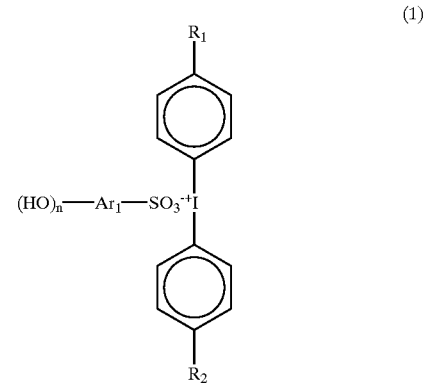

wherein $R_1$ and $R_2$ are respectively H, OH or alkyl or alkoxy group of $C_{1-5}$ and are the same or different, n is an integer from 1 to 3, and $Ar_1$ is a naphthalene unit.

The photosensitive resin used in a composition of the invention is represented by the general formula (2):

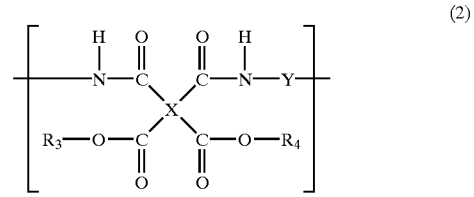

wherein X is a tetravalent aromatic or aliphatic organic radical, Y is a bivalent aromatic or aliphatic organic radical, and $R_3$ and $R_4$ independently are H or a monovalent aliphatic organic protecting group removable by acid.

15 Claims, 1 Drawing Sheet

ION-TYPE PHOTOACID GENERATOR CONTAINING NAPHTHOL AND PHOTOSENSITIVE POLYIMIDE COMPOSITION PREPARED BY USING THE SAME

BACKGROUND OF THE INVENTION

1. Field of the Invention

The present invention relates to an ion-type photoacid generator and a photosensitive polyimide composition. More specifically, the present invention relates to an ion-type photoacid generator containing a naphthol structure, a photosensitive polyimide composition using the photoacid generator, and applications of the composition.

2. Background of the Invention

In the semiconductor device industry, semiconductors and liquid crystal displays (LCDs) with high integration, high density, high reliability, and high-speed properties have been developed and widely used. For these purposes intensive research has been conducted for organic materials which have good processability and high purity. For the organic materials to be used in the semiconductor device industry, the materials should be thermally stabilized at a temperature of 200° C. or above which is required in processes for manufacturing semiconductor devices.

Polyimide is one of the suitable organic materials for this purpose, because it has high heat resistance, good mechanical strength, low dielectric constant, high insulation, high planarity, low impurities and high reliability.

Polyimide is typically prepared by obtaining a polyimide precursor solution through polymerization of a diamine compound and a dianhydride compound in a polar organic solvent such as N-methyl pyrrolidone (NMP), dimethyl acetamide (DMAc) or dimethyl formamide (DMF). The polyimide precursor solution is coated on a silicon wafer or a glass substrate and cured by exposing to heat to form a polyimide film. Commercial polyimide for electronic devices is available in the form of a polyimide precursor solution or polyimide film. Polyimide for semiconductors is available in the form of a polyimide precursor solution.

FIG. 1 is a schematic cross-section of a semiconductor device in which a photosensitive polyimide composition according to the present invention is applied as a buffer coating film. In resin seal large scale integration (LSI), shrinkage of the resin after sealing and thermal stress by a difference in heat expansion coefficients between the resin and the chip can generate cracks on the passivation layer 5 of the chip or damage the wire bonding 2. These problems can be solved by using a polyimide to form a buffer layer between the chip and the sealing material 1. The polyimide layer should be thick to provide a good buffering effect, thereby improving the productivity of semiconductors. It is preferable that the thickness of the polyimide layer is 10 $\mu$m or above.

With reference to FIG. 1, polyimide layer 6 has formed therein via holes, for example to facilitate linkage of electrodes and wire bonding pad 2. To form the via holes, a method of coating a photoresist on the polyimide layer 6 and then etching the polyimide layer has been widely used. However, recently photosensitive polyimides have been tried for application.

When a conventional non-photosensitive polyimide is used, an etching process is required to form holes by using a photoresist for wire bonding and connecting between metal wires. However, when a photosensitive polyimide is used, the lithography process using a photoresist can be omitted, and a buffer coating process can be reduced up to about 50%, resulting in high productivity and reduced manufacturing cost. Accordingly, intensive research has been conducted concerning the application of photosensitive polyimides to the semiconductor industry.

U.S. Pat. No. 3,957,512 to Kleeberg et al. discloses a method for preparation of relief structures by forming a film or a foil from a poly-addition or poly-condensation prepolymer. A photosensitive prepolymer solution is applied to a substrate to form a film, and the coated substrate is exposed to ultraviolet. On the exposed part, photopolymerization is performed to form a cross-linked structure. The unexposed part is dissolved or stripped off by an organic solvent and the relief structure which remains is annealed to remove the photosensitive organic radical during imide reaction. Finally a polyimide pattern is obtained.

U.S. Pat. No. 4,243,743 to Hiramoto et al. discloses a photosensitive composition comprising a precursor of a heat resistant polymer having carboxylic groups and a compound having a photosensitive olefin double bond and an amino or quaternary ammonium salt. The photosensitive polyimide of the patent is easily prepared and has less harmful byproducts.

Further, it has been known that positive-type photosensitive polyimides have more excellent properties than negative-type photosensitive polyimides. Generally speaking, positive-type photosensitive polyimides have better resolution than negative-type. And as the photo-irradiation area is relatively small in the positive-type, a better productivity is provided.

As the positive-type photosensitive polyimides use an alkali aqueous solution as a developing solution, it does not cause any serious problem in environmental pollution. However, the negative type photosensitive polyimides cause several problems in cost and environmental pollution such as wastewater disposal, because an organic solvent such as NMP or DMAc is employed. In spite of the above advantages of the positive-type photosensitive polyimides, they have not been commercially developed due to reasons of other technical difficulties.

Conventional techniques associated with positive-type photosensitive polyimides include a method of blending a polyamic acid as a polyimide precursor with a naphtoquinone diazide compound as a dissolution inhibitor which is patterned by the solubility difference between the exposed portion and the unexposed portion (Japanese Patent Publication Nos. 4-204945 and 6-73003), a method of blending a soluble polyimide having a hydroxyl group with a naphtoquinone diazide compound (Macromolecules, 23, 4796–4802, 1990), and a method of esterification of a polyimide precursor with an o-nitrobenzyl ester group as a photosensitive group (Japanese Patent Publication No. 60-37550).

The foregoing conventional techniques have various problems respectively. In JP Publication Nos. 4-204945 and 6-73003, it is difficult to obtain high resolution because the solubility difference is not sufficient. In Macromolecules (23, 4796–4802, 1990), polyimide precursors are limited in their structure, and physical properties such as transparency are poor. In JP Publication No. 60-37550, the sensitivity of the polymer is too low.

A photoacid generator is one of the important components of a photoresist using a chemical amplification process. Photoacid generators are classified as ion type and non-ion type. The ion type photoacid generators include an iodonium salt (JP Application No. 3-154059, a sulfonium salt and an ammonium salt (U.S. Pat. No. 4,069,055). The ion type photoacid generators are good for acid generation compared to the non-ion type generators, but have low solubility and poor stability. The non-ion type generator is an organic sulfonic acid ester, therefore stability is excellent, but acid generation is poor compared to the ion type generator.

Japanese Patent Publication No. 3-154059 discloses a photoacid generator having a dimethoxyanthracene structure that is applied to a photoresist for i-line. The photoacid generator has poor solubility and too high an UV absorption. Therefore if the generator is used in excess, the transparency is lowered.

Due to the above-mentioned shortcomings, it is difficult to obtain a pattern having a desired resolution when a prior photoacid generator is applied to a photosensitive polyimide, a photosensitive polybenzoxazole composition for a semiconductor passivation layer or a buffer coat layer, or a photoresist composition for build-up PCB (Printed Circuit Board).

Accordingly, the present inventors have developed a photoacid generator having a naphthol structure, which shows improved thermal stability, excellent solubility due to the hydroxyl group included in the naphthol structure, low absorption, and high acid generation efficiency. Further the inventors have developed a photosensitive polyimide composition prepared by using the photoacid generator, which can provide a positive type pattern having high resolution.

SUMMARY OF THE INVENTION

A feature of a preferred embodiment of the present invention is the provision of a photoacid generator with improved thermal stability, excellent solubility due to the hydroxyl group of a naphthol structure, low absorption and high acid-generation efficiency.

A further feature of a preferred embodiment of the present invention is the provision of a photoacid generator that is easily synthesized with high purity easily, and mass-produced economically due to the low prices of the materials to be used.

A further feature of a preferred embodiment of the present invention is the provision of a photoacid generator with high acid generation efficiency as well as low absorption, and a photosensitive polyimide composition which can make a pattern having high resolution to the extent that the aspect ratio is at least 2 on a film having a thickness of more than about 10 microns.

The above and other features and advantages of the preferred embodiments of the present invention may be attained by the detailed descriptions presented below.

In accordance with one aspect of a preferred embodiment of the present invention, a photosensitive resin composition is provided that includes a photosensitive resin and a photoacid generator.

The photoacid generator according to the present invention is represented by the general formula (1):

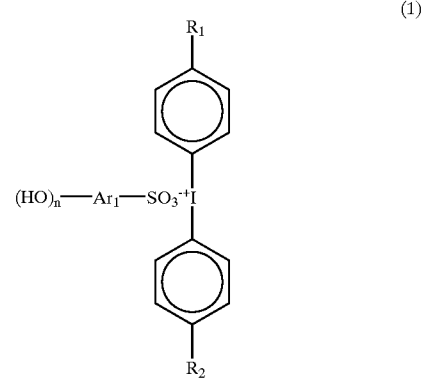

wherein $R_1$ and $R_2$ are respectively H, OH or alkyl or alkoxy group of $C_{1-5}$ and are the same or different, n is integer from 1 to 3, and $Ar_1$ is a naphthalene unit.

The photosensitive resin useful in a composition according to a preferred embodiment of the present invention is represented by the general formula (2):

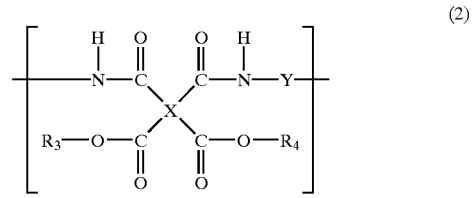

wherein X is a tetravalent aromatic or aliphatic organic radical, Y is a bivalent aromatic or aliphatic organic radical, and $R_3$ and $R_4$ independently are H or a monovalent aliphatic organic protecting group removable by acid.

BRIEF DESCRIPTION OF THE DRAWING

The above and other features and advantages of the present invention will become more apparent by describing in detail the preferred embodiment of the present invention with reference to the attached drawing in which.

Figure 1:
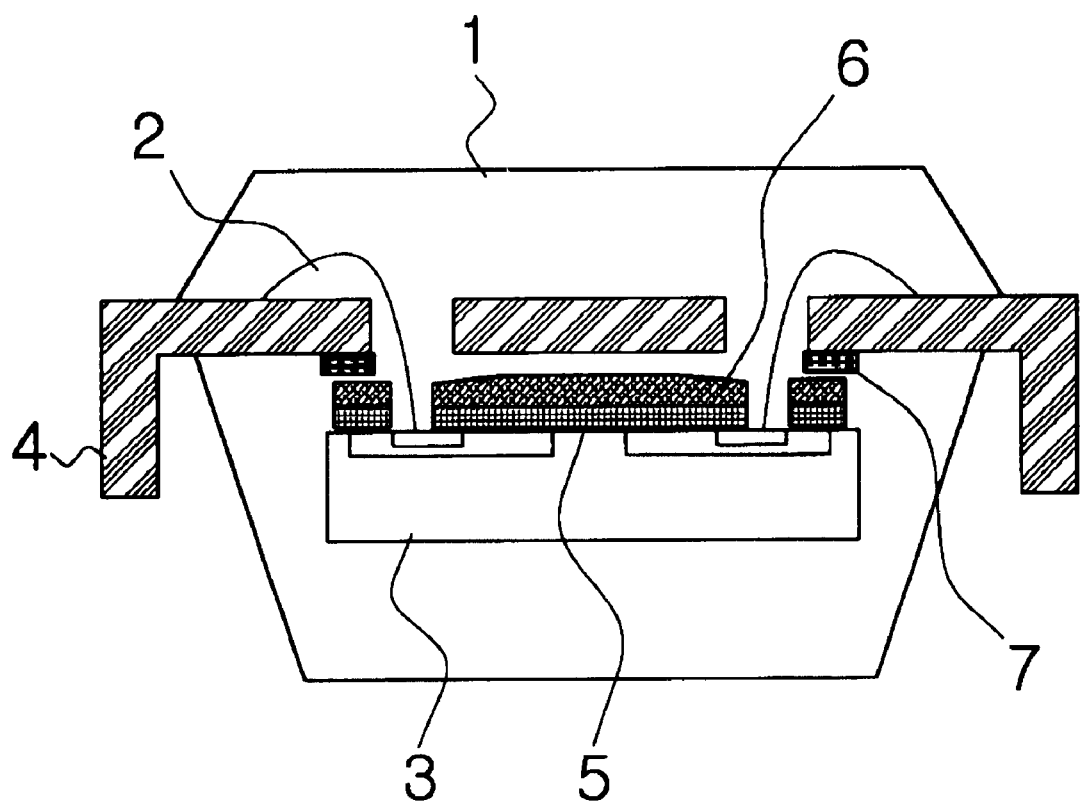
FIG. 1 is a schematic cross-section of a semiconductor device in which a photosensitive composition is employed as a buffer coating film. In the drawing, reference numerals are defined as follows.

1: epoxy sealing material
2: wire bonding
3: LSI chip
4: lead frame
5: passivation layer
6: polyimide
7: LOC tape

DETAILED DESCRIPTION OF THE PREFERRED EMBODIMENTS

Korean Patent Application No. 1999-64662, filed Dec. 29, 1999, is incorporated herein in its entirety by reference.

The present invention relates to a photoacid generator, which generates acid by being dissociated by UV irradiation, and to a photosensitive polyimide composition prepared by using the photoacid generator.

The photoacid generator according to the present invention has excellent properties when it is applied to a photoresist for i-line using a source of light of 365 nm.

The photoacid generator of the present invention, which includes a naphthol structure in the form of an organic salt, is represented by the following formula (1),

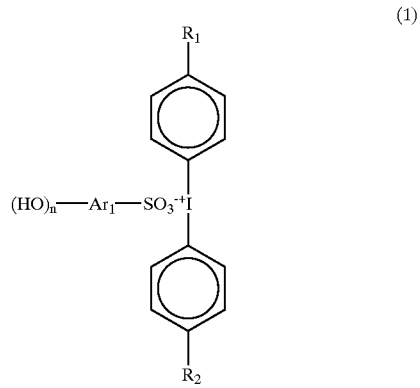

(1)

wherein $R_1$ and $R_2$ are respectively H, OH or alkyl or alkoxy group of $C_{1-5}$ and are the same or different, n is an integer from 1 to 3, and $Ar_1$ is a naphthalene unit.

The photoacid generator represented by the general formula (1), in the form of organic salt, includes a cation portion and an anion portion.

Exemplary specific embodiments of the anion portion $(HO)_n$—$Ar_1$—$SO_3^-$ in the photoacid generator represented by the formula (1) include the following:

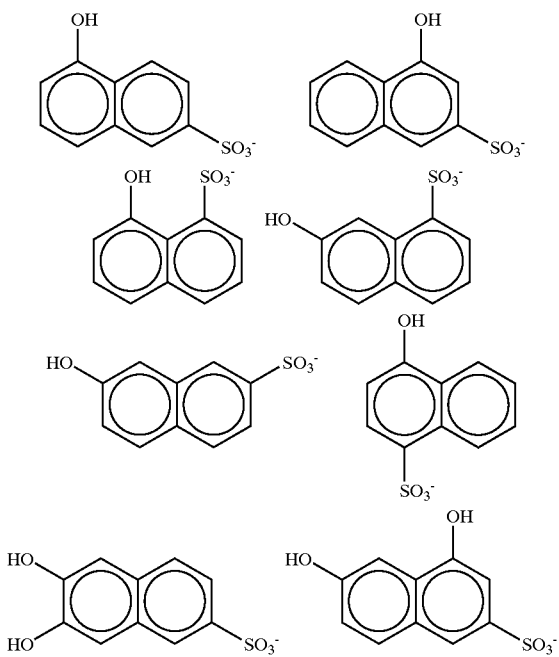

Exemplary specific embodiments of the cation part in the photoacid generator represented by the formula (1) include the following:

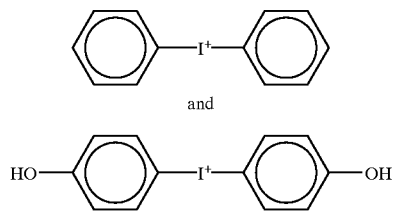

The photoacid generator of the present invention in which a naphthalene structure is introduced has improved thermal stability, excellent solubility due to the hydroxyl group(s), and high acid generation efficiency and low absorption in the area near 365 nm.

The photoacid generator is employed in an amount of about 1–40% by weight, preferably about 5–30% by weight based on the weight of solid contents of the resin. If the photoacid generator is used in too small an amount, photosensitivity is decreased, and if the photoacid generator is used in too great an amount, the transparency of the resin composition is decreased, resulting in difficulty in forming patterns.

The photoacid generator represented by the formula (1) is synthesized easily and with relatively high purity by an ion-exchange reaction between a naphthol sulfonic acid sodium salt and a diphenyliodonium chloride in distilled water.

Preferable examples of the naphtholsulfonic acid sodium salt employed as a cation portion are selected from the group consisting of 1-naphthol-5-sulfuric acid sodium salt, 1-naphthol-3-sulfuric acid sodium salt, 1-naphthol-6-sulfuric acid sodium salt, 1-naphthol-8-sulfuric acid sodium salt, 2-naphthol-8-sulfuric acid sodium salt, 2-naphthol-7-sulfuric acid sodium salt, 1-naphthol-4-sulfuric acid sodium salt, 1,7-dihydroxynaphthalene-3-sulfuric acid sodium salt, and 2,3-dihydroxynaphthalene-6-sulfuric acid sodium salt.

Preferable examples of the naphtholsulfonic acid sodium salt employed as an anion portion include diphenyliodonium chloride and dihydroxyphenyl iodonium chloride.

The photoacid generator represented by formula (1) is employed to prepare a photosensitive resin composition such as a photoresist for processing of semiconductor fine circuits, a photosensitive polyimide used as a passivation layer or a buffer coat layer in a semiconductor, a photosensitive polybenzoxazole and a photoresist for build-up PCB (Printed Circuit Board).

Examples of said photoacid generator used to prepare a photosensitive polyimide composition will be described hereafter.

The photoacid generators according to the present invention can be used alone or in a combination of two or more.

In the present invention, the photosensitive polyimide resin useful in a composition which employs said photoacid generator is represented by formula (2):

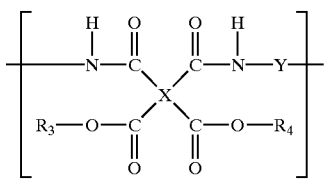
(2)

wherein X is a tetravalent aromatic or aliphatic organic radical, Y is a bivalent aromatic or aliphatic organic radical, and $R_3$ and $R_4$ independently are H or a monovalent aliphatic organic protecting group removable by acid.

In exemplary specific embodiments of the formula (2), X corresponding to the tetravalent aromatic organic radical is as follows:

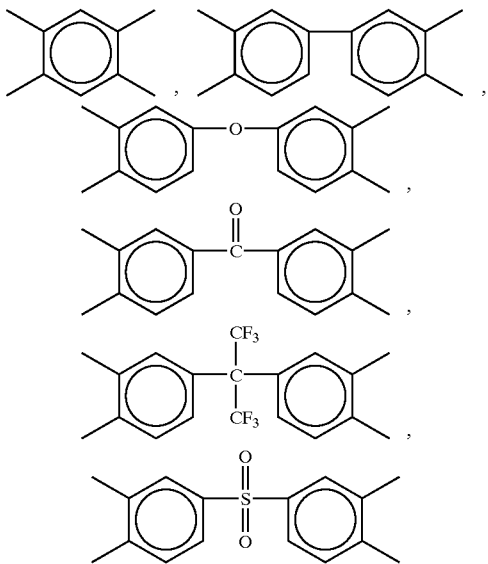

The tetravalent aromatic organic radical preferably is prepared from the tetra carboxylic dianhydride represented by the formula (3):

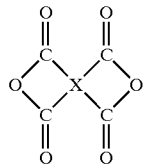
(3)

Preferably the compound represented by the formula (3) includes pyromellitic dianhydride, 3,3,4,4-biphenyl tetracarboxylic dianhydride, 4,4-oxydiphthalic dianhydride 3,3',4,4'-benzophenone tetracarboxylic dianhydride, 2,2-bis(3,4-benzenedicarboxylic anhydride)perfluoropropane and 4,4-sulfonyldiphthalic dianhydride, and at least two of them can also be used simultaneously.

In formula (2), Y is a bivalent aromatic or aliphatic organic radical, which preferably is prepared from a diamine represented by formula (4):

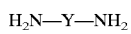
$H_2N-Y-NH_2$ (4)

Preferred exemplary embodiments of the diamine represented by the formula (4) include m-phenylenediamine, p-phenylenediamine, 4,4'-diaminodiphenylmethane, 4,4'-diaminodiphenylether, 2,2'-bis(4-aminophenyl)propane, 4,4'-diaminodiphenylsulfone, 3,3',4,4'-diaminodiphenylsulfone, 4,4'-diaminodiphenylsulfide, 1,4-bis(3-aminophenoxy)benzene, 1,4-bis(4-aminophenoxy)benzene, 1,4-bis(m-aminophenylsulfonyl)benzene, 1,4-bis(p-aminophenylsulfonyl)benzene, 2,2-bis[4-(4-aminophenoxy)phenyl]propane, bis[4-(4-aminophenoxy)phenyl]methane, bis[3,5-dimethyl-4-(4-aminophenoxy)phenyl]methane, bis[4-(4-aminophenoxy)phenyl]sulfone and 2,2'-bis[4-(4-aminophenoxy)phenyl]perfluoropropane. More preferably, 4,4'-diaminodiphenylether, 2,2'-bis(4-aminophenyl)propane and 4,4'-diaminodiphenylsulfone are used. At least two of the diamines can also be used simultaneously.

In formula (2), $R_3$ and $R_4$ independently are H or a protective radical linked to a carboxyl group as a functional radical removable by acid, which includes a t-butoxycarbonyl group, a tetrahydropyranyl group, a trimethysilyl group, and a methylethylether group. When "a" is the average number of H and "b" is the average number of protecting group linked to a carboxyl group in the entire photosensitive polyimide resin, respectively, the value of b/(a+b) is the ratio of the protecting group to the photosensitive resin, and preferably is in the range of about 0.3–0.8. The dissolution rate of the polyimide precursor in tetramethylammonium hydroxide aqueous solution used as a developing solution depends on the ratio between the functional radicals and is controlled.

The positive working photosensitive resin composition according to the present invention is prepared from a polyamic acid ester and a photoacid generator having a naphthalene structure. The photoacid generator is employed in an amount from about 5 to 40%, preferably about 10 to 30% by weight based on the weight of solid contents of the polyimide precursor. If the photoacid generator is added in an amount less than about 5% by weight, the photosensitivity of the composition is deteriorated and if it is added in an amount more than about 40% by weight, the mechanical properties of the film after curing are not good.

The polyamic acid ester and photoacid generator are dissolved in a polar solvent in the above-mentioned ratio to produce a photoresist composition. The solid contents in the composition, namely, the contents of the polyamic acid ester and the photoacid generator, are determined by the thickness of the film to be produced. Typically the solid concentration is controlled in the range of about 5–45% by weight. If the solid concentration is more than about 45% by weight, a spin-coating process is difficult due to high viscosity. The polar solvent preferably is selected from the group consisting of N-methyl-2-pyrrolidone, N,N'-dimethylacetamide, dimethylformamide, dimethylsulfoxide, acetonitrile, diglyme, γ-butyrolactone, phenol, toluene and cyclohexanone, and N-methyl-2-pyrrolidone is preferable.

The positive working photosensitive resin composition of the present invention uses an alkaline aqueous solution as a developing agent. The alkaline developing agent is better than organic solvents in terms of environmental protection and manufacturing cost. Examples of the alkaline developing agent include a quaternary ammonium aqueous solution such as tetramethylammonium hydroxide and tetraethylammonium hydroxide, and an amine aqueous solution such as ethanolamine and propylamine. Tetramethylammonium hydroxide 2.38% aqueous solution is most preferable.

The photosensitive resin composition of the present invention can be applied to a substrate such as a glass plate or a silicon wafer by a known means to obtain a patterned heat-resistant silicon-containing polyimide film. The coating means include spin coat, bar coat and screen printing; typically spin coating is employed to form a buffer coat layer as the composition of the present invention is used. The thickness of the film is in the range of about 0.5–20 μm and the resolution of film is reduced depending on the thickness of the layer.

The resultant coating film preferably is prebaked at a temperature of about 50–120° C. for about 4–10 minutes to remove most of the solvent from the coated film. Afterwards, a photomask whose desirable pattern is formed is placed on this coated film, followed by exposure to lights. The exposure of the irradiating lights preferably is about 200–1,000 mJ/cm$^2$. After exposure, a PEB (post exposure baking) process continues at a temperature of about 60–120° C. for about 30–600 seconds for the film.

In the exposed portion, protected acid-labile groups are removed by acid produced by the photoacid generator, and the dissolution rate of the exposed portion increases evidently depending on that of the unexposed portion in the alkaline developing agent. The dissolution rate difference between the exposed and unexposed portions causes the exposed portion to be rapidly removed and a pattern to be formed. The pattern formed by development using a developing agent is rinsed in a solvent such as alcohol or distilled water and dried, and then can be in the form of a precursor of polyimide.

Resolution of a photosensitive resin is represented as aspect ratio (=a/b), which is the ratio of a formed pattern thickness (a) to line width (b). The photosensitive polyimide composition according to the present invention can achieve high resolution to the extent that the aspect ratio is more than 3.0 due to the photoacid generator represented by formula (1). Namely, in case that the thickness of the film is 15 μm, a pattern is provided with a line width of at least 5 μm. The pattern of polyimide precursor prepared in this manner is converted to a polyimide pattern by heat treatment. Heat treatment preferably is conducted at a temperature of about 150–450° C. under vacuum or a nitrogen stream for about 0.5–5 hours, stepwise or continuously. During the heat treatment, polyamic acid or polyamic acid ester as polyimide precursor is cured and converted to polyimide, with relatively low molecular weight.

A polyimide layer produced from a photosensitive polyimide composition according to the present invention functions as an insulating layer in various electronic devices, such as an insulating layer between layers, a buffer coating film, a passivation film, or an insulating layer of a multi-layer PCB in semiconductor devices.

The present invention will be further described by the following examples, and these examples will not limit the scope of the present invention, which is defined solely by the appended claims.

EXAMPLES

Synthesis of Photoacid Generator

1. Synthesis of Photoacid Generator (DINS-1)

10.83 g of 1-naphthol-5-sulfuric acid sodium salt and 500 ml of distilled water were poured into a 1 L flask and stirred at a temperature of more than 80° C. until solid contents were dissolved completely. In this manner, 12.66 g of diphenyliodonium chloride and 500 ml of distilled water were poured into another 1 L flask, followed by stirring at more than 80° C., and they were dissolved completely. The resulting diphenyliodonium chloride aqueous solution was slowly added to the 1-naphthol-5-sulfuric acid sodium salt solution and then powder formed at the time of mixing. The reactants were filtered under pressure and the resultant powder was separated, followed by washing with distilled water, and dried under vacuum for 48 hours. A resulting photoacid generator (DINS-1) was synthesized.

2. Synthesis of Photoacid Generator (DINS-2)

The photoacid generator (DINS-2) was synthesized in the same manner as the above DINS-1 synthesis except that 1-naphthol-4-sulfuric acid sodium salt was used instead of 1-naphthol-5-sulfuric acid sodium salt.

Synthesis of Photosensitive Polyimide Precursor

1. Synthesis of Photosensitive Polyimide Precursor (PAE-1)

In a 500 ml four hollow containing flask equipped with a thermometer, a stirrer, a nitrogen-injection tube and a cooler, 14.01 g (0.07 mole) of oxydianiline (ODA) was dissolved in 150 ml of N-methyl-2-pyrrolidone (NMP) under nitrogen stream. To the resulting solution was added 21.72 g of oxydiphthalic anhydride (ODPA). Polymerization was carried out for 5 hours at room temperature and polyamic acid was obtained. 150 ml of NMP was added to the solution, followed by cooling to −10° C. Further, 11.33 g of triethylamine was added and then 11.91 g of chloromethylethylether was slowly added to the solution by dropping. The reaction was carried out at −10° C. for 2 hours. After the reaction, the reactants were filtered under pressure, followed by removal of salts produced. The filtrate without salt was slowly added to 3 L of distilled water to precipitate the reactants. The resulting precipitate was filtrated and dried for 24 hours at 40° C. and a photosensitive polyimide precursor powder (PAE-1) was synthesized.

2. Synthesis of Photosensitive Polyimide Precursor (PAE-2)

The photosensitive polyimide precursor (PAE-2) was synthesized in the same manner as the above PAE-1 synthesis except that a mixture of 13.03 g of ODPA and 12.36 g of biphthalic anhydride (BPDA) was used instead of 21.72 g of ODPA as dianhydride.

Example 1

A photosensitive polyimide composition was prepared by dissolving a mixture of 10 g of the above photosensitive polyimide precursor powder (PAE-1) and 8 g of DINS-1 as a photoacid generator in 40 g of N-methyl-2-pyrrolidone (NMP) and filtering the solution through a 0.2 μm filter.

Resolution

A 4-inch silicon wafer was coated with the photosensitive resin composition by spin-coating, and then heated at 80° C. for 6 minutes and 100° C. for 2 minutes on a hot plate. The spin was adjusted so that the thickness of the polyimide precursor film would be 15 μm on the silicon wafer. Next, the coating film, which was adhered closely to a photomask was exposed to ultraviolet light of 365 nm from a high pressure mercury arc lamp (1000 mJ/cm$^2$). After the exposure, the film was heated for 3 minutes on a hot plate at 100° C. (hereinafter this treatment is called "PEB (post exposure baking)"), followed by developing the film with 2.38 wt % of tetramethylammonium hydroxide (TMAH) aqueous solution as a developing solution for 3 minutes, rinsing with distilled water and drying. A pattern having a clearly remaining unexposed portion was obtained. The coated silicon wafer was baked under nitrogen at 80° C. for 10 minutes, and at 120° C. for 60 minutes, and further at 350° C. for 60 minutes. A film having pattern of at least 5 μm of line width×10 μm of thickness was prepared. The test results of the resolution are shown in Table 1.

Physical Properties of Film

A silicon wafer was coated with the photosensitive polyimide precursor composition by spin coating, and then baked under nitrogen at 80° C. for 10 minutes, and at 120° C. for 60 minutes, and further at 350° C. for 60 minutes on a hot plate. The spin was adjusted so that the thickness of the polyimide film would be 10 μm on the silicon wafer. PCT (pressure cooking treatment) was carried out at 125° C. and 2.3 atm for 1 hour in an autoclave to take off the polyimide film from the silicon wafer. Properties such as tensile strength were determined using the film in a 1 cm width. The properties of the film were as follows: tensile strength was 100 MPa, modulus was 2.6 GPa and elongation rate was 6%.

Example 2

A photosensitive polyimide composition was prepared by dissolving a mixture of 10 g of the above photosensitive polyimide precursor powder (PAE-2) and 8 g of DINS-2 as a photoacid generator in 40 g of N-methyl-2-pyrrolidone (NMP) and filtering the solution through a 0.2 μm filter.

Resolution

A film having pattern of at least 6 μm of line width×10 μm of thickness was prepared. The test of the resolution was carried out in the same manner as in Example 1. The test results are shown in Table 1.

Physical Properties of Film

The test of the properties of the obtained film was carried out in the same manner as in Example 1. The properties of the film were as follows: tensile strength was 130 MPa, modulus was 3.0 GPa and elongation rate was 10%.

Comparative Example

Instead of DINS-1 as a photoacid generator, a conventional photoacid generator (DIAS) was mixed with photosensitive polyimide precursor (PAE-1) in amounts of 10 and 20% by weight, respectively, and the resulting composition was exposed to irradiating light of 1,000 mJ/cm$^2$. The test results are given in Table 1 Transparency of PAE-1 before adding the photoacid generator was 62%.

TABLE 1

| | Photo acid generator | | | |
| --- | --- | --- | --- | --- |
| | DIAS | | DINS-1 | |
| Structural formula | (ε = 8,500) | | (ε = 260) | |
| content (wt % to base resin) | 10 | 20 | 10 | 20 |
| dissolution rate of exposed portion | 40 | 3300 | 600 | 3500 |
| Transparency (10 μm of thickness) | 10 | 1 | 55 | 49 |
| maximum film thickness in 5 μm of L/S | — | 7 | — | 15 |
| resolution (aspect ratio) | — | 1.4 | — | 3 |

DIAS structural formula: anthracene with OCH$_3$ groups at 9,10-positions and SO$_3^-$ $^+$IPh$_2$ substituent.

DINS-1 structural formula: naphthalene with HO– and –SO$_3^-$ $^+$IPh$_2$ substituents.

In the above, the present invention was described based on the specific preferred embodiments and the attached drawings, but it should be apparent to those ordinarily skilled in the art that various changes and modifications can be added without departing from the spirit and scope of the present invention which will be defined in the appended claims.

What is claimed is:

1. A photosensitive resin composition comprising:

(a) a photosensitive base resin; and (b) a photoacid generator represented by the formula (1)

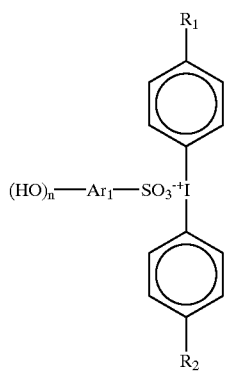

wherein $R_1$ and $R_2$ are respectively H, OH or alkyl or alkoxy group of $C_{1-5}$ and are the same or different, n is integer from 1 to 3, and $Ar_1$ is a naphthalene unit.

2. The photosensitive resin composition of claim 1, in which said photosensitive base resin is a polyimide precursor represented by the formula (2):

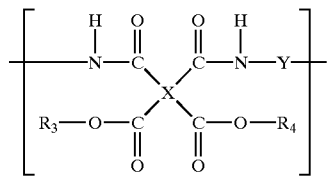

wherein X is a tetravalent aromatic or aliphatic organic radical, Y is a bivalent aromatic or aliphatic organic radical, and $R_3$ and $R_4$ independently are H or a monovalent aliphatic organic protecting group removable by acid.

3. The photosensitive resin composition of claim 2, in which said tetravalent aromatic organic radical is selected from the group consisting of:

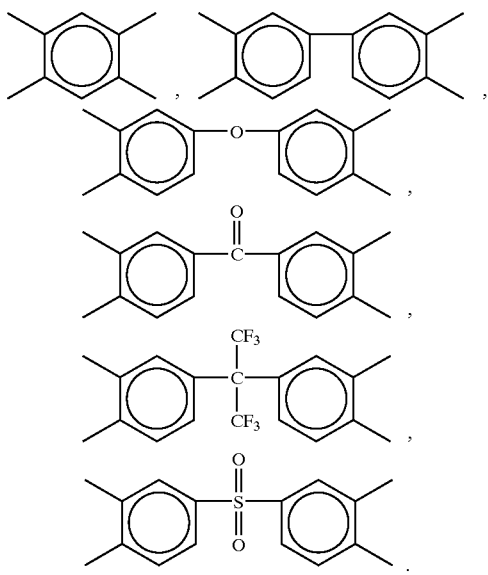

4. The photosensitive resin composition of claim 2, in which said tetravalent aromatic organic radical is a derivative of a tetracarboxylic dianhydride represented by the formula (3):

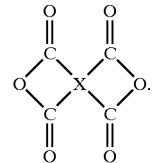

5. The photosensitive resin composition of claim 4, in which said tetracarboxylic dianhydride is selected from the group consisting of pyromellitic dianhydride, 3,3,4,4-biphenyl tetracarboxylic dianhydride, 4,4-oxydiphthalic dianhydride 3,3',4,4'-benzophenone tetracarboxylic dianhydride, 2,2-bis(3,4-benzenedicarboxylic anhydride) perfluoropropane and 4,4-sulfonyldiphthalic dianhydride.

6. The photosensitive resin composition of claim 2, in which at least two polyimide precursors, each including a different tetravalent aromatic or aliphatic organic radical, are included.

7. The photosensitive resin composition of claim 2, in which Y is a derivative of a diamine represented by the formula (4):

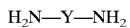

8. The photosensitive resin composition of claim 7, in which said diamine is selected from the group consisting of m-phenylenediamine, p-phenylenediamine, 4,4'-diaminodiphenylmethane, 4,4'-diaminodiphenylether, 2,2'-bis(4-aminophenyl)propane, 4,4'-diaminodiphenylsulfone, 3,3',4,4'-diaminodiphenylsulfone, 4,4'-diaminodiphenylsulfide, 1,4-bis(3-aminophenoxy)benzene, 1,4-bis(4-aminophenoxy)benzene, 1,4-bis(m-aminophenylsulfonyl)benzene, 1,4-bis(p-aminophenylsulfonyl)benzene, 2,2-bis[4-(4-aminophenoxy)phenyl]propane, bis[4-(4-aminophenoxy)phenyl]methane, bis[3,5-dimethyl-4-(4-aminophenoxy)phenyl]methane, bis [4-(4-aminophenoxy)phenyl]sulfone, and 2,2'-bis[4-(4-aminophenoxy)phenyl]perfluoropropane.

9. The photosensitive resin composition of claim 8, in which said diamine is selected from the group consisting of 4,4'-diaminodiphenylether, 2,2'-bis(4-aminophenyl)propane, 4,4'-diaminodiphenylsulfone.

10. The photosensitive resin composition of claim 7, in which at least two of said diamines are employed.

11. The photosensitive resin composition of claim 1, in which said photosensitive base resin and said photoacid generator are dissolved in a polar solvent to prepare a photoresist composition, and said photoacid generator is employed in an amount from about 1 to about 40% by weight based on the weight of solid contents of the base resin.

12. The photosensitive resin composition of claim 11, in which said polar solvent is selected from the group consisting of N-methyl-2-pyrrolidone, N,N'-dimethylacetamide, dimethylformamide, dimethylsulfoxide, acetonitrile, diglyme, γ-butyrolactone, phenol, toluene and cyclohexanone.

13. A photoacid generator represented by the formula (1):

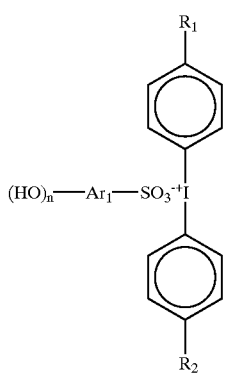

wherein $R_1$ and $R_2$ are respectively H, OH or alkyl or alkoxy group of $C_{1-5}$ and are the same or different, n is integer from 1 to 3, and $Ar_1$ is a naphthalene unit.

14. The photoacid generator of claim 13, in which said anion portion, $(HO)_n$—$Ar_1$—$SO_3^-$ is selected from the group consisting of:

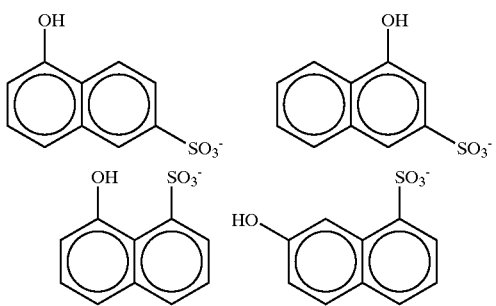

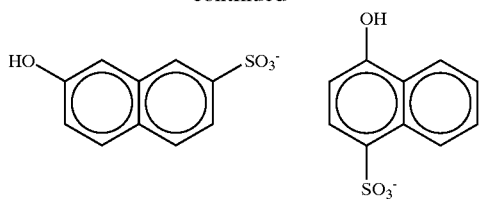

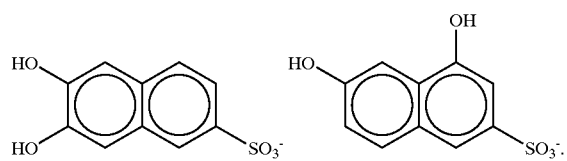

15. The photoacid generator of claim 13, in which said cation portion is selected from the group consisting of

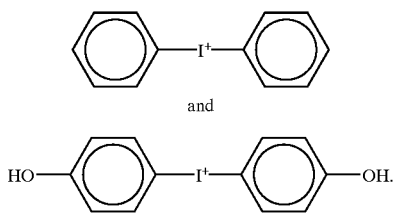

* * * * *